United States Patent
Ono et al.

[11] Patent Number: 5,856,374
[45] Date of Patent: Jan. 5, 1999

[54] CURABLE COMPOSITION

[75] Inventors: Toru Ono; Masatugu Kusano; Masataka Himeno; Shigeki Yuasa, all of Tokuyama, Japan

[73] Assignee: Tokuyama Corporation, Tokuyama, Japan

[21] Appl. No.: 962,035

[22] Filed: Oct. 31, 1997

[30] Foreign Application Priority Data

Nov. 1, 1996 [JP] Japan ..................................... 8-291527

[51] Int. Cl.$^6$ .............................. A61K 6/083; C08K 3/34; C08K 3/36; C08K 3/22
[52] U.S. Cl. ......................... 523/116; 523/115; 523/220; 523/223; 524/783; 524/786; 524/789
[58] Field of Search .................................... 523/115, 116, 523/230, 117, 223; 524/783, 786, 789

[56] References Cited

U.S. PATENT DOCUMENTS 5,350,782  9/1994  Sasaki et al. ............................ 523/116
5,356,951  10/1994  Yearn et al. ............................ 523/116

*Primary Examiner*—Peter A. Szekely
*Attorney, Agent, or Firm*—Sherman and Shalloway

[57] ABSTRACT

A curable composition comprising (i) a polymerizable monomer, (ii) irregular-shaped inorganic particles (A) having an average particle diameter of from 1 to 9 μm, and containing particles having particle diameters of not smaller than 10 μm in an amount of not larger than 3% by weight, such as silica-zirconia irregular-shaped particles, (iii) spherical inorganic particles (B) having an average particle diameter of from 0.1 to 5 μm, such as spherical silica-zirconia particles; (iv) inorganic fine particles (C) having an average particle diameter of from 0.01 to 0.1 μm, such as fine particles of at least one inorganic oxide selected from the group consisting of silica, alumina, silica-zirconia and silica-titania; and (v) a polymerization initiator; wherein the irregular-shaped inorganic particles (A), spherical inorganic particles (B) and inorganic fine particles (C) are used in a total amount of from 300 to 1900 parts by weight per 100 parts by weight of the polymerizable monomer, and, when the total amount of the spherical inorganic particles (B) and the inorganic fine particles (C) is set to be 100% by weight, the spherical inorganic particles (B) are used at a ratio of from 50 to 99% by weight and the inorganic fine particles (C) are used at a ratio of from 50 to 1% by weight, and wherein the weight ratio [(A)/{(B)+(C)}] of the irregular-shaped inorganic particles (A) to the total amount of the spherical inorganic particles (B) and the inorganic fine particles (C) is from 0.3 to 3, and the polymerization initiator is used in an amount of from 0.01 to 5 parts by weight per 100 parts by weight of the polymerizable monomer.

10 Claims, 1 Drawing Sheet

FIG.1

CURABLE COMPOSITION

BACKGROUND OF THE INVENTION

1. (Field of the Invention)

The present invention relates to a curable composition that can be favorably used as a dental composite restorative. More specifically, the invention relates to a curable composition which forms a cured product that features very high mechanical strength and, particularly, a very high fracture toughness value and a very high bending strength.

2. (Prior Art)

In recent years, a composite restorative has been much used as a restoring material in the dental field since it imparts a color equivalent to that of natural tooth and it can be easily handled. The restorative is generally used in a manner that a cavity in a tooth is directly filled with the restorative and is polymerized, and is cured by such a polymerization means as irradiation with light to restore the tooth. The restored part accomplished by the above-mentioned method has a relatively low mechanical strength. Therefore, this restoring method is generally effected for the portions where mechanical strength is not much required.

Recently, however, the composite restorative has been used even for restoring posterior teeth etc. that receive the pressure of occlusion. For instance, a mold of the cavity of a tooth is filled with the curable composition which is then polymerized upon the irradiation with light or by heating for a sufficient period of time, so that the composition is adhered to the cavity.

However, the restored portion obtained by polymerizing the curable composition according to the above-mentioned method, has a strength smaller than that of a natural tooth, and is broken at the edges due to a strong pressure of occlusion.

In order to solve this problem, it has been reported that a technology has been developed for obtaining a curable composition containing a filler at an increased density by using an inorganic powder having dissimilar particle sizes at a particular mixing ratio, or for blending a polymerizable monomer with irregular-shaped inorganic particles having particular particle diameters and properties and with spherical inorganic particles having particular particle diameters at particular ratios (Japanese Patent Laid-Open No. 132102/1991) and a method of obtaining a high mechanical strength by mixing spherical inorganic particles having particles of the order of submicrons and inorganic fine particles having particle diameters of from 0.01 to 0.1 µm and further by using the highly dispersed mixture particles as a filler (Japanses Patent Laid-Open No. 12305/1996). The cured products obtained by these method and technology, however, have bending strengths which are smaller than 250 MPa. There has been no curable composition available that was capable of forming a cured product having a bending strength greater than 270 MPa possessed by the dentin of a tooth.

Besides, according to a report by Fujishima et al., "The Journal of the Japanese Society for Dental Materials and Devices, Vol. 13, No. 4, pp. 375–380, 1994", the breaking toughness value ($K_{1C}$) which is an important property related to the breakage of the composite restorative is as low as 2.28 Mpa·m$^{1/2}$ at the greatest.

SUMMARY OF THE INVENTION

It is an object of the present invention to provide a curable composition which is capable of forming a cured product having a high fracture toughness value and a bending strength that could not be accomplished with the dental composite restoratives produced according to the prior art.

In order to reach the above-mentioned object, the present inventors have conducted a keen study, and have discovered the fact that the above object can be accomplished when irregular-shaped inorganic particles having particular particle diameters, spherical inorganic particles having particle diameters of from submicrons to several microns, and inorganic fine particles of from 0.01 to 0.1 µm are mixed together, and when a polymerizable monomer is blended with the obtained highly dispersed mixture particles at a particular ratio, and have thus accomplished the present invention.

That is, the present invention is concerned with a curable composition comprising:

(i) a polymerizable monomer;

(ii) irregular-shaped inorganic particles (A) having an average particle diameter of from 1 to 9 µm, and containing particles having particle diameters of not smaller than 10 µm in an amount of not larger than 3% by weight;

(iii) spherical inorganic particles (B) having an average particle diameter of from 0.1 to 5 µm;

(iv) inorganic fine particles (C) having an average particle diameter of from 0.01 to 0.1 µm; and (v) a polymerization initiator;

wherein the irregular-shaped inorganic particles (A), spherical inorganic particles (B) and inorganic fine particles (C) are used in a total amount of from 300 to 1900 parts by weight per 100 parts by weight of the polymerizable monomer, and, when the total amount of the spherical inorganic particles (B) and the inorganic fine particles (C) is set to be 100% by weight, the spherical inorganic particles (B) are used in an amount of from 50 to 99% by weight and the inorganic fine particles (C) are used in an amount of from 50 to 1% by weight, and wherein the weight ratio [(A)/{(B)+(C)}] of the irregular-shaped inorganic particles (A) to the total amount of the spherical inorganic particles (B) and the inorganic fine particles (C) is from 0.3 to 3, and the polymerization initiator is used in an amount of from 0.01 to 5 parts by weight per 100 parts by weight of the polymerizable monomer.

DETAILED DESCRIPTION OF THE INVENTION

There is no particular limitation on the polymerizable monomer used in the present invention, and any monomer can be used that has been used for dental applications. A representative example that is generally favorably used is a polymerizable monomer having an acryloyl group and/or a methacryloyl group. Concrete examples are as described below.

a) Monofunctional Vinyl Monomers.

Methacrylates such as methyl methacrylate, ethyl methacrylate, isopropyl methacrylate, hydroxyethyl methacrylate, tetrahydrofurfuryl methacrylate and glycidyl methacrylate, as well as acrylates corresponding to these methacrylates; and acrylic acid, methacrylic acid, p-methacryloyloxybenzoic acid, N-2-hydroxy-3-methacryloyloxypropyl-N-phenylglycine, 4-methacryloyloxyethyltrimellitic acid and anhydride thereof, 6-methacryloyloxyhexamethylenemalonic acid, 10-methacryloyloxydecamethylenemalonic acid, 2-methacryloyloxyethyldihydrodiene phosphate, 10-methacryloyloxydecamethylenedihydrodiene phosphate, and 2-hydroxyethylhydrodienephenyl phosphonate.

b) Bifunctional Vinyl Monomers.

(I) Aromatic Compounds.

2,2-Bis(methacryloyloxyphenyl) propane, 2,2-bis[4(3-methacryloyloxy)-2-hydroxypropoxyphenyl] propane (hereinafter abbreviated as bis-GMA), 2,2-bis(4-methacryloyloxyphenyl) propane, 2,2-bis(4-methacryloyloxypolyethoxyphenyl) propane (hereinafter abbreviated as D-26E), 2,2-bis(4-methacryloyloxydiethoxyphenyl) propane, 2,2-bis(4-methacryloyloxytetraethoxyphenyl) propane, 2,2-bis(4-methacryloyloxypentaethoxyphenyl) propane, 2,2-bis(4-methacryloyloxydipropoxyphenyl) propane, 2(4-methacryloyloxydiethoxyphenyl)-2(4-methacryloyloxydiethoxyphenyl) propane, 2(4-methacryloyloxydiethoxyphenyl) 2(4-methacryloyloxyditriethoxyphenyl) propane, 2(4-methacryloyloxydipropoxyphenyl)-2-(4-methacryloyloxytriethoxyphenyl) propane, 2,2-bis(4-methacryloyloxypropoxyphenyl) propane, 2,2-bis(4-methacryloyloxyisopropoxyphenyl) propane and acrylates corresponding to these methacrylates; and a diadduct obtained from the addition of a vinyl monomer having a —OH group such as a methacrylate such as 2-hydroxyethyl methacrylate, 2-hydroxypropyl methacrylate, 3-chloro-2-hydroxypropyl methacrylate or an acrylate corresponding to these methacrylates, and a diisocyanate compound having an aromatic group, such as diisocyanate methyl benzene or 4,4'-diphenylmethane diisocyanate.

(II) Aliphatic Compounds.

Ethylene glycol dimethacrylate, diethylene glycol dimethacrylate, triethylene glycol dimethacrylate (hereinafter abbreviated as 3G), butylene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate and acrylates corresponding to these methacrylates; a diadduct obtained from the addition of a vinyl monomer having a -OH group such as a methacrylate such as 2-hydroxyethyl methacrylate, 2-hydroxypropyl methacrylate, 3-chloro-2-hydroxypropyl methacrylate or an acrylate corresponding to these methacrylates, and a diisocyanate compound such as hexamethylene diisocyanate, trimethylhexamethylene diisocyanate, diisocyanate methyl cyclohexane, isophorone diisocyanate, or methylenebis(4-cyclohexyl isocyanate); and acrylic anhydride, methacrylic anhydride, 1,2-bis(3-methacryloyloxy-2-hydroxypropoxy) ethyl, and di(2-methacryloyloxypropyl) phosphate.

c) Trifunctional Vinyl Monomers.

Methacrylates such as trimethylolpropane trimethacrylate, trimethylolethane trimethacrylate, pentaerythritol trimethacrylate, trimethylolmethane trimethacrylate, and acrylates corresponding to these methacrylates.

d) Tetrafunctional Vinyl Monomers.

Diadducts obtained from the addition of a glycidol dimethacrylate and a diisocyanate compound such as pentaerythritol tetramethacrylate, pentaerythritol tetraacrylate, and diisocyanate methyl benzene, diisocyanate methyl cyclohexane, isophorone diisocyanate, hexamethylene diisocyanate, trimethylhexamethylene diisocyanate, methylenebis(4-cyclohexylisocyanate), 4,4'-diphenylmethane diisocyanate, tolylene-2, or 4-diisocyanate.

These polymerizable monomers can be used in a single kind but can be used in two or more kinds being mixed together.

The curable composition of the present invention is partly constituted by the irregular-shaped inorganic particles (A) having an average particle diameter of from 1 to 9 μm and, preferably, from 1.5 to 5 μm, and containing particles having a particle diameter of not smaller than 10 μm in an amount of not larger than 3% by weight and, preferably, not larger than 1% by weight. Any known irregular-shaped inorganic particles can be used without any limitation, provided the above-mentioned requirements are satisfied. When the average particle diameter of the irregular-shaped inorganic particles (A) lies outside the range of from 1 to 9 μm, it becomes difficult to obtain a cured product having a high mechanical strength. When the amount of the particles having a particle diameter of not smaller than 10 μm exceeds 3% by weight, furthermore, the particles having particle diameters of not smaller than 10 μm become start points of destruction, resulting in a decrease in the mechanical strength.

As for the material of the irregular-shaped inorganic particles (A), an inorganic material insoluble in water can be used without any particular limitation. Examples include borosilicate glass, soda glass, glass containing a heavy metal (such as barium, strontium, zirconium), aluminosilicate, glass ceramics, silica, and composite inorganic oxides such as silica-zirconia, silica-titania, silica-alumina and the like.

The curable composition of the present invention is partly constituted by the spherical inorganic particles (B) having an average particle diameter of from 0.1 to 5 μm. Any known spherical inorganic particles can be used without any particular limitation provided the average particle diameter lies within the above-mentioned range. When the average particle diameter of the spherical inorganic particles (B) is smaller than 0.1 μm, filling rate of the inorganic filler in the curable composition decreases resulting in a decrease in the mechanical strength. When the average particle diameter is larger than 5 μm, the surface areas of the spherical inorganic particles decrease per a unit volume of the curable composition, making it difficult to obtain a cured product having a high mechanical strength. When the shape of the particle is not spherical, the filling rate cannot be reached up to a desired range, making it difficult to obtain a cured product having a high mechanical strength.

The spherical inorganic particles (B) need not be of a perfect spherical shape. In general, the powder is photographed by using a scanning-type electron microscope (hereinafter abbreviated as SEM). The powder is usable enough when the average degree of symmetry is not smaller than 0.6, the average degree of symmetry being found by dividing a particle diameter in a direction at right angles with a maximum diameter of a particle observed within a unit visual field by a maximum diameter thereof.

Concrete examples of the spherical inorganic particles (B) that are generally preferably used are inorganic oxides such as amorphous silica, silica-zirconia, silica-titania, silica-titania-barium oxide, quartz, alumina and the like. It is also allowable to use a composite oxide comprising an inorganic oxide containing a small amount of an oxide of a metal of the Group I of periodic table, in order to easily obtain the above-mentioned inorganic oxides in a dense form through firing at a high temperature. When the curable composition of the present invention is to be used for dental applications, it is particularly desired to use a composite oxide comprising chiefly silica and zirconia, since it exhibits X-ray contrast property and makes it possible to obtain a cured product having superior abrasion resistance.

The spherical inorganic particles (B) used in the present invention need not necessarily be those consisting of a single group, provided the average particle diameter lies within the above-mentioned range. The spherical inorganic particles (B) may be a mixture of starting material powders consisting of two or more groups having dissimilar average particle diameters as has been disclosed in, for example, Japanese Patent Publication No. 10603/1991. In this case, the average particle diameter is an average volume particle diameter of mixed particles consisting of a plurality of groups.

Though there is no particular limitation on the particle diameter distribution of the inorganic particles, the curable composition can be favorably handled when the inorganic particles exhibit excellent monodispersion property having a coefficient of variation in the particle diameter of not larger than 0.3.

There is no particular limitation on the method of producing the spherical inorganic particles (B), and any method can be employed provided it is capable of producing the particles having the above-mentioned particle diameter and shape. From the industrial point of view, there is employed a method of production relying upon the hydrolysis of a metal alkoxide. In order to maintain surface stability of the spherical inorganic particles (B), furthermore, it is desired to decrease the silanol groups on the surfaces. For this purpose, means is often preferably employed according to which the spherical inorganic particles (B) are dried and are, then, fired at a temperature of 500° to 1000° C.

The present invention uses the inorganic fine particles (C) having an average particle diameter over a range of from 0.01 to 0.1 $\mu$m. Any known inorganic fine particles can be used without limitation provided the average particle diameter lies within the above-mentioned range. When the average particle diameter of the inorganic fine particles (C) lies outside the above-mentioned range, the filling rate of inorganic material in the curable composition decreases, and the effect of the invention is not exhibited to a sufficient degree.

The inorganic fine particles (C) used in the present invention need not necessarily be those consisting of a single group, provided the average particle diameter lies within the above-mentioned range. The inorganic fine particles (C) may be a mixture of particles consisting of two or more dissimilar groups. In this case, the average particle diameter is an average volume particle diameter of a mixture consisting of a plurality of groups. The particles may be those having a spherical shape or may be irregular-shaped particles. However, use of the particles of a spherical shape is desired from the standpoint of increasing the bending strength and breaking toughness value.

Concrete examples of the inorganic fine particles (C) that are generally preferably used include inorganic oxides such as ultrafine silica, ultrafine alumina, ultrafine zirconia, ultrafine titania, amorphous silica, silica-zirconia, silica-titania, silica-titania-barium oxide, quartz, alumina and the like. It is also allowable to use a composite oxide comprising an inorganic oxide containing a small amount of an oxide of a metal of the Group I of periodic table, in order to easily obtain the above-mentioned inorganic oxides in a dense form through firing at a high temperature.

In the curable composition of the present invention, it is desired that the inorganic filler comprising the irregular-shaped inorganic particles (A), spherical inorganic particles (B) and inorganic fine particles (C), has hydrophobic surfaces from the standpoint of improving dispersion in the polymerizable monomer. There is no particular limitation on the method of rendering the surfaces to be hydrophobic, and any widely known method can be used without limitation. Representative examples of the method of rendering the surfaces to be hydrophobic include a method which uses an organic silicon compound as a hydrophobic property-imparting agent, such as silane coupling agent, e.g., $\gamma$-methacryloyloxyalkyltrimethoxy silane or hexamethyldisilazane, a method which uses a titanate-type coupling agent, or a method which graft-polymerizes the polymerizable monomer on the surfaces of the particles.

The greatest feature of the present invention resides in the use of the above-mentioned three inorganic fillers in combination, i.e., irregular-shaped inorganic particles (A), spherical inorganic particles (B) and inorganic fine particles (C). Examples have been known using the irregular-shaped inorganic particles (A) only, or using the spherical inorganic particles (B) and the inorganic fine particles (C) only in combination. In particular, the example which exhibits a good bending strength by using the spherical inorganic particles (B) and the inorganic fine particles (C) only has been disclosed in Japanese Patent Laid-Open No. 12305/1996. However, though a large bending strength is obtained, the fracture toughness value of the curable composition is not enough. This is attributed to that the breakage propagates. It is presumed that the addition of the irregular-shaped inorganic particles (A) suppresses the propagation of breakage, enabling the fracture toughness value to be enhanced unexpectedly.

In the curable composition of the present invention, it is desired that the irregular-shaped inorganic particles (A), spherical inorganic particles (B) and inorganic fine particles (C) have, in their mixed state, not more than 0.1 cc/g of an integrated volume of micro pores due to strongly aggregated particles that have a micro porous diameter of not smaller than 0.08 $\mu$m.

The micro porous diameter and the micro pores due to strongly aggregated particles are measured by the mercury intrusion porosity method disclosed in Japanese Patent Laid-Open No. 12305/1996. The micropores due to strongly aggregated particles do not exist inside the particles but exist among the particles. According to the mercury intrusion porosity method, in general, the distribution of micro pores is measured by elevating the pressure of mercury to be not lower than 100 MPa. The micro pores formed among the particles having a weak aggregating force collapse due to the intrusion of mercury of a high pressure, and no mercury is expelled out of the micro pores when the pressure is decreased. Therefore, it appears as if the micro pores have extinguished. In the distribution of micro pores obtained under the pressurized condition, micro pores that extinguish when the pressure is being reduced are referred to as micro pores due to weakly aggregated particles. The pores existing in the particles and the micro pores formed among the strongly aggregated particles are not collapsed by the intrusion of mercury of an elevated pressure, and do not extinguish expelling mercury out of the micro pores when the pressure is being reduced. In the distribution of micro pores obtained under the pressurized condition, therefore, the pores that do not extinguish when the pressure is being reduced are called micro pores due to strongly aggregated particles. When pores exist in the primary particles, however, it is difficult to distinguish the strongly aggregated pores from the pores in the primary particles, and the effect of the invention is exhibited difficultly. According to the present invention, therefore, it is desired that no pore exists in the primary particles. Here, the fact that no pore exists in the primary particles is discriminated from that the surface area of the sample is in agreement with the surface area calculated from the particle diameters found from the SEM observation. In this case, the surface area is measured relying upon the BET method described later.

Figure 1:
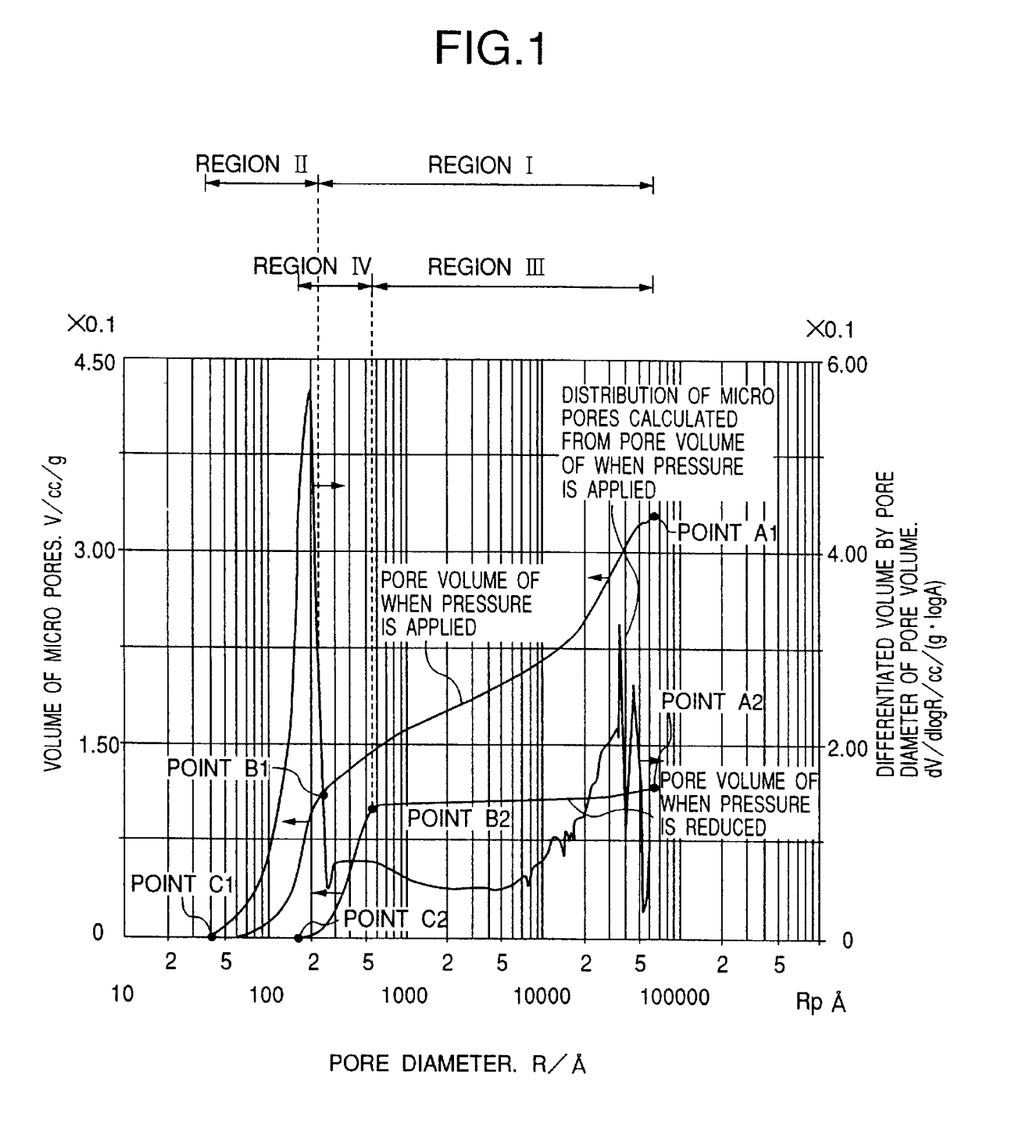
FIG. 1 is a diagram showing the results of the volume of pores and distribution of the porous diameters of an inorganic particle composition used in Example 1 as measured relying upon the mercury intrusion porosity method using the Porosimeter 2000 manufactured by Carlo Erba Co. by increasing or decreasing the pressure in a range of from the atmospheric pressure to 203 MPa (1990 Kgf/cm$^2$).

In the present invention, the volume of the strongly aggregated pores of the mixture of the irregular-shaped inorganic particles (A), spherical inorganic particles (B) and inorganic fine particles (C), is measured as described below and the result is shown as a chart of FIG. 1.

A change in the volume of micro pores under the pressurized condition is divided into a region I (point A1 to point B1) where the corresponding micro porous diameters are large and the distribution of pores is broad, and a region II (point B1 to point C1) where the corresponding porous diameters are small and the distribution of pores is sharp. Similarly, a change in the volume of micro pores when the pressure is reduced is divided into a region III (point A2 to point B2) and a region IV (point B2 to point C2). From the shapes of peaks, volumes of pores and amounts of shift when the pressure is reduced, it will be understood that there exist a correlation between the region I and the region III, and a correlation between the region II and the region IV. Here, the volume of pores that is about 0.22 cc/g (difference of volume of pores between the point A1 and the point B1; hereinafter, the volume of pores is found in the same manner) in the region I under the pressurized condition, almost extinguishes into 0.01 cc/g in the region III when the pressure is reduced. From this, it will be understood that micro pores in the region I are basically due to weakly aggregated particles but there partly exist strongly aggregated pores, and the volume of the strongly aggregated pores of not smaller than 0.08 $\mu$m is not larger than 0.01 cc/g which is smaller than the volume in the region III. This satisfies the requirement of the inorganic composition of the present invention in that the volume of the strongly aggregated pores having porous diameters of not smaller than 0.08 $\mu$m in the inorganic composition is not larger than 0.1 cc/g with respect to the inorganic composition as shown in the measurement of FIG. 1. Additionally, the pores of the region II do not almost disappear when they are in the region IV. From this fact, the pores is considered to be due to strongly aggregated particles.

There is no particular limitation in the method of setting the integrated volume of the strongly aggregated pores to lie within the above-mentioned range. Generally, however, there is preferably employed a method which is capable of digesting the aggregation of particles and mixing them together to a sufficient degree. Concretely speaking, the particles are digested and mixed by using an ultra-high pressure shock-type emulsion dispersion device or a homogenizer. A desired volume of strongly aggregated pores can be obtained by selecting the conditions such as amount of samples, concentrations, treating time, etc.

There is no particular limitation on the polymerization initiator that is used in the present invention, and any known polymerization initiator can be used without limitation. In general, the kind of the polymerization initiator is determined depending upon the means for polymerizing the polymerizable monomer. The polymerization means may be the one utilizing light energy such as ultraviolet rays or visible rays, the one based upon the reaction of a peroxide with a promoting agent, or the one based upon the heating. The polymerization means will be selected depending upon the need. In the case of the reaction based on the light energy (hereinafter referred to as photo-polymerization), the polymerization initiator will preferably be a known one such as $\alpha$-diketone-reducing agent, ketal-reducing agent or thioxanthone-reducing agent. Examples of the $\alpha$-diketone include camphorquinone, benzil, 2,3-pentadione, and 3,4-heptadione. Examples of the ketal include benzyldimethyl ketal, benzyldiethyl ketal, and benzyl(2-methoxyethyl ketal). Examples of the thioxanthone include thioxanthone, 2,4-dimethylthioxanthone, 2,4-diethylthioxanthone and 2-chlorothioxanthone.

Examples of the reducing agent which is a component of the photo-polymerization initiator include tertiary amines such as 2-(dimethylamino) ethyl methacrylate, ethyl-4-dimethylamino benzoate, and N-methyldiethanolamine; aldehydes such as laurylaldehyde, dimethylaminobenzaldehyde, and terephthalaldehyde; and sulfur-containing compounds such as 2-mercaptobenzoxazole, 1-decanethiol, thiosalicylic acid and thiobenzoic acid.

In the case of the thermal polymerization, a generally employed peroxide or an azo compound is used as the polymerization initiator. Concrete examples include known polymerization initiators such as organic peroxides, e.g., dicumyl peroxide, di-p-chlorobenzoyl peroxide, benzoyl peroxide, and dilauroyl peroxide, as well as azo compounds, e.g., 2,2'-azobisisobutylonitrile, 4,4'-azobis(4-cyanovaleric acid), 2,2'-azobis(2,4-dimethyl valeronitrile), etc.

The polymerization initiator is blended in amounts over a range known per se. without any limitation. In general, the polymerization initiator is used at a ratio of from 0.01 to 5 parts by weight per 100 parts by weight of the polymerizable monomer.

In the curable composition of the present invention, the amount of the inorganic filler comprising the irregular-shaped inorganic particles (A), spherical inorganic particles (B) and inorganic fine particles (C) must be from 300 to 1900 parts by weight and, preferably, from 500 to 1200 parts by weight per 100 parts by weight of the polymerizable monomer. Furthermore, the irregular-shaped inorganic particles (A), spherical inorganic particles (B) and inorganic fine particles (C) are blended at ratios as described below. First, when the total amount of the spherical inorganic particles (B) and inorganic fine particles (C) is set to be 100% by weight, the spherical inorganic particles (B) are used in an amount of from 50 to 99% by weight and, preferably, from 60 to 90% by weight, and the inorganic fine particles (C) are used in an amount of from 50 to 1% by weight and, preferably, from 40 to 10% by weight. The weight ratio [(A)/{(B)+(C)}] of the irregular-shaped inorganic particles (A) to the amount of the total amount of the spherical inorganic particles (B) and the inorganic fine particles (C) is from 0.3 to 3 and, preferably, from 0.4 to 2.3.

When the amount of the inorganic filler comprising the irregular-shaped inorganic particles (A), spherical inorganic particles (B) and inorganic fine particles (C) is smaller than the above-mentioned range with respect to 100 parts by weight of the polymerizable monomer, the filling rate is not sufficient and it is difficult to obtain a cured product having a high mechanical strength. When the amount is greater than the above-mentioned range, on the other hand, the inorganic filler does not uniformly disperse in the polymerizable monomer, and the mechanical strength becomes small.

As for the mixing ratio of the spherical inorganic particles (B) and the inorganic fine particles (C), when the amount of the spherical inorganic particles (B) is smaller than 50% by weight, the amount of the inorganic fine particles (C)

exceeds 50% by weight, and the curable composition loses the mechanical strength after it is polymerized and cured. Even when the amount of the spherical inorganic particle (B) exceeds 99% by weight, the curable composition loses the mechanical strength after it is polymerized and cured.

When the above-mentioned weight ratio [(A)/{(B)+(C)}] of the irregular-shaped inorganic particles (A) to the total amount of the spherical inorganic particles (B) and inorganic fine particles (C) is smaller than 0.3 or is larger than 3, it becomes difficult to obtain a cured product having a high mechanical strength despite the total amount satisfies the above-mentioned range.

The curable composition of the present invention can be blended with widely known additives within a range in which the effect is not conspicuously impaired. Examples of the additive will be polymerization inhibitor, pigment, ultraviolet ray-absorbing agent and the like.

An optimum method of curing the curable composition of the present invention may be selected depending upon the kind of the polymerization initiator. When, for example, a polymerization initiator for photopolymerization is used, it is, generally, desired to project light for not less than 10 seconds and, preferably, for 30 seconds to one hour and, then, to effect the heating at a temperature of 80° to 120° C. for 10 minutes to 20 hours in order to obtain a cured product having a high mechanical strength.

When a polymerization initiator for heat polymerization is used, furthermore, it is desired to effect the heating at 60° to 200° C. and, particularly, at 80° to 120° C. for 10 minutes to 20 hours and, particularly, for 15 minutes to one hour. In this case, it is desired that the polymerization is conducted in an atmosphere such as an inert gas such as nitrogen or helium, or water vapor.

According to the present invention, it is desired that a curable composition comprises a polymerizable monomer; irregular-shaped inorganic particles (A) composed chiefly of silica-zirconia and having an average particle diameter of from 1 to 9 $\mu$m and containing particles having particle diameters of not smaller than 10 $\mu$m in an amount of not larger than 3% by weight; spherical inorganic particles (B) composed chiefly of silica-zirconia and having an average particle diameter of from 0.1 to 5 $\mu$m; and inorganic fine particles (C) composed chiefly of at least one inorganic oxide selected from the group consisting of silica, alumina, silica-zirconia and silica-titania and having an average particle diameter of from 0.01 to 0.1 $\mu$m; wherein the irregular-shaped inorganic particles (A), spherical inorganic particles (B) and inorganic fine particles (C) are used in a total amount of from 500 to 1200 parts by weight per 100 parts by weight of the polymerizable monomer, and, when the total amount of the spherical inorganic particles (B) and the inorganic fine particles (C) is set to be 100% by weight, the amount of the spherical inorganic particles (B) is from 60 to 90% by weight and the amount of the inorganic fine particles (C) is from 40 to 10% by weight, the weight ratio [(A)/{(B)+(C)}] of the total amount of the spherical inorganic particles (B) and the inorganic fine particles (C) to the irregular-shaped inorganic particles (A) is from 0.67 to 1.5, and the integrated volume of the strongly aggregated pores having pore diameters of not smaller than 0.08 $\mu$m is not larger than 0.1 cc/g in a state where the irregular-shaped inorganic particles (A), spherical inorganic particles (B) and inorganic fine particles (C) are being mixed together. The above curable composition can be favorably handled and the cured product thereof exhibits very excellent fracture toughness value, bending strength and good color.

The curable composition of the present invention makes it possible to obtain a cured product having a high fracture toughness value and a high bending strength equivalent to that of a natural tooth. In the dental applications, a metal restorative such as an inlay restorative or a crown restorative has so far been used at portions where a high pressure of occlusion is exerted. It is, however, made possible to use the curable composition of the present invention in place of the metal restoratives to restore the tooth maintaining color which is little different from that of a natural tooth. Moreover, the curable composition of the present invention can be used in the applications other than the dental restorative without any limitation.

[EXAMPLES]

The present invention will now be concretely described by way of Examples to which only, however, the invention is in no way limited. In the following Examples and Comparative Examples, properties of the inorganic particles were measured, the paste of the curable composition was prepared and cured, and the mechanical strength of the cured product was measured, in accordance with the methods described below.

(1) Particle diameter and coefficient of variation in the particle diameter.

The powder was photographed using the SEM, the number of particles and the particle diameter observed within a unit visual field of the photograph were found, and an average volume diameter of the starting material particles was found in accordance with the following formula and was regarded to be an average particle diameter. A coefficient of variation in the particle diameter was also calculated. In the case of a mixture consisting of two or more groups having different average particle diameters, the average volume particle diameter was calculated relying upon a weighed mean of the average particle diameters of the groups and the amounts of addition.

$$\text{Ave. particle diameter:} \quad \overline{X} = \sqrt[3]{\frac{\sum_{i=1}^{n} X_i^3}{n}} \quad \text{(average volume diameter)}$$

$$\text{Coefficient of variation} = \frac{\sigma_{n-1}}{\overline{Y}}$$

$$\overline{Y} = \frac{\sum_{i=1}^{n} X_i}{n} \quad \text{(Number average diameter)}$$

$$\sigma_{n-1} = \sqrt{\frac{\sum_{i=1}^{n} (X_i - \overline{Y})^2}{n-1}}$$

where, n: number of particles observed $X_i$: particle diameter of the i-th particle (2) Average degree of symmetry of particles.

The powder was photographed using the SEM, and the number (n) of particles observed within a unit visual field of the photograph, a maximum diameter (long diameter Li) of the particle and a diameter (short diameter Bi) in the direction at right angles with the long diameter, were found, and the average degree of symmetry of the particles was calculated in accordance with the following formula, $$\text{Average degree of symmetry} = \frac{\sum_{i=1}^{n} Bi/Li}{n}$$

(3) Distribution of particle sizes.

The distribution of particle sizes was measured by using a laser diffraction-type particle size distribution measuring apparatus (SALD-1100 manufactured by Shimazu Seisakusho Co.).

(4) Porous diameter and distribution of pores.

About 0.2 g of the sufficiently dried particles were weighed and were measured for their porous diameter and the distribution of pores by using a pore distribution measuring apparatus which is based on the mercury intrusion porosity method (Porosimeter 2000 manufactured by Carlo Erba Co.).

(5) Specific surface area.

Measured by using the FlowSobe II-2300 manufactured by Micrometrics Co. The principle of measurement is based on the BET method.

(6) Preparation of a paste of a curable composition and method of curing.

A photopolymerization initiator was added at a predetermined ratio to the polymerizable monomer to prepare a matrix monomer. Next, the inorganic filler and the matrix monomer were introduced into an agate mortar, and were sufficiently kneaded in a dark place to prepare a homogeneous curable composition paste.

The curable composition paste was introduced into the molds for taking measurements, and was cured upon irradiation with light to a sufficient degree. The cured products were taken out from the molds, and were further polymerized at 100° C. for 20 minutes. Thereafter, the cured products were immersed in water maintained at 37° C. for 24 hours and were used as test pieces.

(7) Fracture toughness value.

A square pole-like test piece measuring 2 mm wide×4 mm high×20 mm long was prepared, and a crack of about 2 mm was formed in the direction of height by using a cutter to obtain a three-point bending test piece having a notch formed on one side thereof. The test piece was mounted on a tester (Autograph 500D manufactured by Shimazu Seisakusho Co.), a three-point bending test was conducted maintaining a distance of 16 mm between the fulcrums and at a crosshead speed of 1.0 mm/min, in order to calculate a breaking toughness value from the breaking strength.

(8) Bending strength.

A square pole-like test piece measuring 2×2×25 mm was mounted on a tester (Autograph 5000D manufactured by Shimazu Seisakusho Co.), and a three-point bending strength was measured at a crosshead speed of 0.5 mm/min.

(Preparation Examples 1 to 3)

Preparation of irregular-shaped inorganic particles (A).

60 Milliliters of 0.005% dilute sulfuric acid was added to a solution obtained by dissolving 1600 g of a tetraethyl silicate (produced by Colcoat Co., Ltd.) in 2.0 liters of isobutanol at room temperature, and was stirred for 3 hours to effect partial hydrolysis, followed by the addition of 670 g of tetrabutyl zirconate and 77 g of sodium methylate. After stirred for one hour, 0.3 liters of water was added thereto with stirring to further effect the hydrolysis thereby to obtain a gel. The gel was taken out, dried by heating at 100° C. to remove the solvent, thereby to obtain a dry gel. The dry gel was coarsely pulverized by a ball mill into a size of not larger than 1000 μm. The thus pulverized product was further pulverized using a jet mill (Model FS-4, produced by Seishin Kigyo Co.) under the condition of a nozzle pressure of 6 kg/cm². The pulverized product was fired at 940° C. for one hour to obtain a white powder. From the X-ray diffraction and fluorescent X-ray analysis, the white powder was irregular-shaped inorganic particles of a composite oxide of zirconium, silicon and sodium partly containing crystals of the tetragonal system of zirconia.

Three kinds of irregular-shaped inorganic particles (A-1, A-2, A-3) were obtained from the white powder relying upon the hydraulic elutriation. The obtained particles were further treated for their surfaces with γ-methacryloyloxypropyl trimethoxysilane. In the measurement of porous diameters of the irregular-shaped inorganic particles and the distribution of pores, neither the pores in the particles nor the strongly aggregated pores were observed. Table 1 shows the average particle diameters of the irregular-shaped inorganic particles and the contents of particles having particle diameters of not smaller than 10 μm.

TABLE 1

| Irregular-shaped particles (A) | A-1 | A-2 | A-3 | A-4 |
|---|---|---|---|---|
| average particle diameter (μm) | 3.4 | 3.0 | 0.8 | 2.9 |
| amounts of particles having particle diameters of not smaller than 10 μm (% by wt.) | 1.0 | 4.5 | 0.0 | 0.6 |

(Preparation Example 4)

Preparation of irregular-shaped inorganic particles (A).

Irregular-shaped inorganic particles were prepared according to the Preparation Example 1, and a white powder (A-4) of the type of $SiO_2$—$ZrO_2$—$Na_2O$ was obtained by the same method as that of the Preparation Examples 1 to 3 but using a tetraisopropyl silicate instead of the tetraethyl silicate and effecting the stirring for 4 hours after the addition of the dilute sulfuric acid. From the X-ray diffraction and fluorescent X-ray analysis, the white powder was comprised of irregular-shaped inorganic particles of a composite oxide of zirconium, silicon and sodium partly containing crystals of the tetragonal system of zirconia.

The particles were further treated for their surfaces with γ-methacryloyloxypropyl trimethoxysilane. Neither the pores in the particles nor the strongly aggregated pores were observed in the obtained irregular-shaped inorganic particles. Table 1 shows the average particle diameters and the contents of particles having particle diameters of not smaller than 10 μm.

(Preparation Example 5)

Synthesis of spherical silica-zirconia particles (B) having an average particle diameter of 0.5 μm.

80 Grams of a tetraethyl silicate (product name, Ethyl silicate 28 produced by Colcoat Co., Ltd.) and 400 g of an isobutyl alcohol (produced by Tonen Sekiyu Kagaku K.K.) were mixed together and to which was added 5 g of 0.05% dilute sulfuric acid. The mixture was stirred at 40° C. for about one hour and was hydrolyzed. To this solution was then added, with stirring, a solution obtained by dissolving 35 g of a tetrabutyl zirconate (produced by Nippon Soda Co., Ltd.) and 5 g of a sodium methylate methanol solution (concentration of 28% by weight) in 200 g of an isobutyl alcohol, in order to prepare a mixture solution of tetraethyl silicate and tetrabutyl zirconate. Next, 4 g of the tetraethyl silicate was added, with stirring, to an ammoniacal alcohol solution into which have been introduced 1000 g of isobutyl alcohol and 250 g of 25% ammonia water in a 3-liter glass container equipped with a stirrer. The mixture was stirred for 30 minutes, and to which was dropwisely added a mixture solution of the tetraethyl silicate and the tetrabutyl zirconate over a period of about 6 hours. During the reaction, the temperature of the reaction vessel was maintained at 40° C. After the reaction, the solvent was distilled off from the cloudy solution in the reaction vessel, and the reaction product was dried and fired at 950° C. for one hour to obtain silica-zirconia particles (B-1). The silica-zirconia particles possessed an average particle diameter of 0.52 μm, an average degree of symmetry of 0.96 and a coefficient of variation in the particle diameter of 0.13. The theoretical surface area of 4.8 m$^2$/g as found from the average particle diameter was in good agreement with the specific surface area of 4.8 m$^2$/g based upon the BET method, and no pore was recognized in the particles. Table 2 shows the physical properties.

TABLE 2

| Spherical inorganic particles (B) | B-1 | B-2 | B-3 | B-4 |
|---|---|---|---|---|
| Main component | silica-zirconia | silica | silica | silica |
| Average particle diameter (μm) | 0.52 | 0.62 | 1.89 | 11.2 |
| Average degree of symmetry | 0.96 | 0.97 | 0.98 | 0.95 |
| Coefficient of variation | 0.13 | 0.05 | 0.03 | 0.07 |
| Calculated surface area (m$^2$/g) | 4.8 | 4.4 | 1.4 | 0.12 |
| Specific surface area (m$^2$/g) | 4.8 | 4.5 | 1.1 | 0.10 |

(Preparation Examples 6 to 8)

Synthesis of spherical silica particles (B).

10 Grams of a tetraethyl silicate (product name, Ethyl silicate 28 produced by Colcoat Co., Ltd.) was added, with stirring, to an ammoniacal alcohol solution into which have been introduced 400 g of methyl alcohol and 100 g of 25% ammonia water in a 3-liter glass container equipped with a stirrer. The mixture was stirred for 30 minutes, and to which were dropwisely and simultaneously added 2000 g of the tetraethyl silicate and 640 g of 25% ammonia water maintaining the solution temperature in the reaction vessel at 30° C. over a period of about 4 hours. After the reaction, the solvent was distilled off from the cloudy solution in the reaction vessel, and the reaction product was dried and fired at 1000° C. for one hour to obtain silica particles (B-2). The silica particles possessed an average particle diameter of 0.62 μm, an average degree of symmetry of 0.97 and a coefficient of variation in the particle diameter of 0.05. The specific surface area based on the BET method was 4.5 m$^2$/g which was in fair agreement with the theoretical specific surface area of 4.4 m$^2$/g calculated from the average particle diameter, and from which it was learned that no pore existed in the particles. On the other hand, silica particles (B-3) were obtained through the same operation as the one described above but using the ethyl alcohol instead of the methyl alcohol in the initial ammoniacal alcohol solution. Furthermore, silica particles (B-4) were obtained through the same operation as the one described above but using 300 g of ethyl alcohol and 150 g of 25% ammonia water instead of 400 g of ethyl alcohol and 100 g of 25% ammonia water in the initial ammoniacal alcohol solution, and using 800 g of ammonia water instead of 640 g of 25% ammonia water in the next step. Properties of the silica particles were as shown in Table 2.

(Preparation Example 9)

Synthesis of spherical silica-titania particles (C) having an average particle diameter of 0.08 μm.

170 Grams of a tetraethyl silicate (product name, Ethyl silicate 28 produced by Colcoat Co., Ltd.) and 400 g of methanol were mixed together and to which was added 5 g of an aqueous solution containing 0.04% of hydrochloric acid. The mixture was stirred at 30° C. for about one hour and was hydrolyzed. To this solution was then added, with stirring, a solution obtained by dissolving 20 g of a tetrabutyl titanate (produced by Nippon Soda Co., Ltd.) and 10 g of a sodium methylate methanol solution (concentration of 28% by weight) in 200 g of an isopropyl alcohol, in order to prepare a mixture solution of tetraethyl silicate and tetrabutyl titanate. Next, 2 g of the tetraethyl silicate was added, with stirring, to an ammoniacal alcohol solution into which have been introduced 1000 g of methanol and 250 g of 25% ammonia water in a 3-liter glass container equipped with a stirrer. The mixture was stirred for 30 minutes, and to which was dropwisely added a mixture solution of the tetraethyl silicate and the tetrabutyl titanate over a period of about 5 hours. During the reaction, the temperature of the reaction vessel was maintained at 40° C. After the reaction, the solvent was distilled off from the cloudy solution in the reaction vessel, and the reaction product was dried and fired at 950° C. for one hour to obtain silica-titania particles (C-1). The silica-titania particles possessed an average particle diameter of 0.077 μm and a spherical shape. The theoretical surface area of 33.9 m$^2$/g as found from the average particle diameter was in good agreement with the specific surface area of 32.5 m$^2$/g based upon the BET method, and no pore was recognized in the particles. Table 3 shows the physical properties.

TABLE 3

| Inorganic fine particles (C) | C-1 | C-2 | C-3 |
|---|---|---|---|
| Main component | silica-titania | silica-zirconia | silica |
| Average particle diameter (μm) | 0.077 | 0.058 | 0.01 |
| Theoretical surface area (m$^2$/g) | 33.9 | 43.1 | 200 |
| Specific surface area (m$^2$/g) | 32.5 | 47.4 | 200 |

(Preparation Example 10)

Synthesis of spherical silica-zirconia particles (C) having an average particle diameter of 0.06 μm.

A tetraethyl silicate was added into the ammoniacal alcohol solution of preparation Example 5, and a mixture solution of the tetraethyl silicate and tetrabutyl zirconate was added thereto in the step of Preparation Example 5, in order to obtain silica-zirconia particles (C-2) in the same manner as in Preparation Example 5 but using 100 g of methyl alcohol and 200 g of 25% ammonia water as an ammoniacal alcohol solution, and dropwisely adding the whole amount of the mixture solution of a tetraethyl silicate and a tetrabutyl zirconate over a period of about 3 hours instead of adding 4 g of the tetraethyl silicate alone. The silica-zirconia particles possessed an average particle diameter of 0.058 μm and a spherical shape. The theoretical surface area of 43.1 m²/g as found from the average particle diameter was in good agreement with the specific surface area of 47.4 m²/g based on the BET method, and no pore was recognized in the particles. Physical properties were as shown in Table 3.

Inorganic fine particles (C) other than those used in the foregoing preparation examples and their abbreviations are as described below. C-3: Fine powdery silica (Reolosil QS102, specific surface area 200 m²/g, produced by Tokuyama Co.).

(Preparation Example 11)

70 Grams of the spherical silica-zirconia particles (B-1) having an average particle diameter of 0.52 μm and 30 g of the spherical silica-titania particles (C-1) having an average particle diameter of 0.077 μm were introduced into 400 g of pure water solvent and were dispersed by using a nanomizer which is a dispersing machine of the type of giving a shock under super high pressure of 60 MPa. The particles were treated for their surfaces with the γ-methacryloyloxypropyl trimethoxysilane. Then, the solvent was distilled off to obtain a mixture of particles.

The above mixture of particles and the irregular-shaped inorganic particles (A-1) having an average particle diameter of 3.4 μm and containing particles of not smaller than 10 μm in an amount of 1.0% by weight were introduced into a mortar at a weight ratio [(A-1)/{(B-1) +(C-1)}] of 1.0, and were gently mixed and dispersed to obtain an inorganic filler (M-1) which was then measured for its distribution of porous diameters. As a result, the volume of the strongly aggregated pores having a pore diameter of not smaller than 0.08 μm was 0.01 cc/g. Table 4 shows the composition of the inorganic filler (M-1) and the volume of the strongly aggregated pores.

(Preparation Examples 12 to 20)

Inorganic fillers (M-2 to M-10) were obtained in the same manner as in Preparation Example 11 but changing the compositions of the spherical inorganic particles (B), inorganic fine particles (C) and irregular-shaped inorganic particles (A) to be blended as shown in Table 4. The volumes of the strongly aggregated pores of the inorganic fillers were as shown in Table 4.

Blending amount 1: Blending amount (% by weight) of the spherical inorganic particles (B) of when the total amount of the spherical inorganic particles (B) and the inorganic fine particles (C) is set to be 100% by weight.

Blending amount 2: Blending amount (% by weight) of the inorganic fine particles (C) of when the total amount of the spherical inorganic particles (B) and the inorganic fine particles (C) is set to be 100% by weight.

Blending amount 3: Weight ratio [(A)/{(B)+(C)}] of the irregular-shaped inorganic particles (A) to the total amount of the spherical inorganic particles (B) and the inorganic fine particles (C)

(Example 1)

Spherical silica-zirconia particles (B-1) having an average particle diameter of 0.52 μm and spherical silica-titania particles (C-1) having an average particle diameter of 0.077 μm were mixed and dispersed together, and were treated for their surfaces to obtain a mixture of particles. The thus obtained mixture of particles and irregular-shaped inorganic particles (A-1) having an average particle diameter of 3.4 μm and containing particles of not smaller than 10 μm in an amount of 1.0% by weight, were mixed together to prepare an inorganic filler (M-1). 10 Grams of the inorganic filler (M-1) was introduced into a mortar, and to which was gradually added a matrix monomer bis-GMA/3G (weight ratio of 60/40) in which have been dissolved a camphorquinone and a dimethylaminobenzoic acid ethyl ester as a polymerization initiator and as a reducing agent in amounts of 0.5%, respectively, until a paste-like consistency was exhibited. The content of the inorganic filler (M-1) was 640 parts by weight per 100 parts by weight of the matrix monomer. The paste was polymerized and cured upon irradiation with light, and was further polymerized by heating, and was measured for its breaking toughness value and bending strength. The fracture toughness value was 3.1 Mpa·m$^{1/2}$ and the bending strength was 274 MPa. Table 5 shows the blending ratios of the inorganic filler (M-1) per 100 parts by weight of the matrix monomer and the mechanical properties.

(Examples 2 to 4)

Curable compositions were obtained in the same manner as in Example 1 but changing the inorganic filler to be

TABLE 4

| Inorganic fillers | Compositions of inorganic fillers | | | | | | Volume of micro pores due to strongly aggregated particles (cc/g) |
|---|---|---|---|---|---|---|---|
| | Spherical inorganic particles (B) | Blending amount 1 (% by weight) | Inorganic fine particles (C) | Blending amount 2 (% by weight) | Irregular-shaped inorganic particles (A) | Blending amount 3 | |
| M-1 | B-1 | 70 | C-1 | 30 | A-1 | 1.0 | 0.01 |
| M-2 | B-2 | 80 | C-2 | 20 | A-4 | 1.5 | 0.02 |
| M-3 | B-1 | 90 | C-3 | 10 | A-1 | 1.0 | 0.02 |
| M-4 | B-3 | 70 | C-1 | 30 | A-1 | 1.0 | 0.01 |
| M-5 | B-1 | 100 | — | — | A-1 | 1.0 | 0.01 |
| M-6 | — | — | C-1 | 100 | A-1 | 1.0 | 0.04 |
| M-7 | B-1 | 70 | C-1 | 30 | A-2 | 1.0 | 0.01 |
| M-8 | B-1 | 70 | C-1 | 30 | A-3 | 1.0 | 0.01 |
| M-9 | B-1 | 70 | C-1 | 30 | — | — | 0.02 |
| M-10 | B-4 | 70 | C-1 | 30 | A-1 | 1.0 | 0.01 |

In Table 4, the blending amounts 1, 2 and 3 are as described below.

blended as shown in Table 5. The curable compositions were polymerized and cured upon irradiation with light and were further polymerized by heating to evaluate their mechanical properties. Table 5 shows the blending ratios of the inorganic fillers per 100 parts by weight of the matrix monomer and mechanical properties.

TABLE 5

| Example No. | Kind of inorganic filler | Blending ratio inorganic filler (pts. by wt.) | Fracture toughness value (Mpa · m$^{1/2}$) | Bending strength (Mpa) |
| --- | --- | --- | --- | --- |
| 1 | M-1 | 640 | 3.1 | 274 |
| 2 | M-2 | 625 | 3.1 | 275 |
| 3 | M-3 | 576 | 2.8 | 251 |
| 4 | M-4 | 619 | 3.0 | 265 |
| 5 | M-1 | 669 | 3.2 | 278 |

(Example 5)

The procedure was carried out in the same manner as in Example 1 but changing the matrix monomer into D-2.6E/ 3G (weight ratio of 70/30). Table 5 shows the blending ratio of the inorganic filler per 100 parts by weight of the matrix monomer and mechanical properties.

(Comparative Example 1)

A curable composition was obtained in the same manner as in Example 1 but using the inorganic filler (M-5) instead of the inorganic filler (M-1). Table 6 shows a blending ratio of the inorganic filler (M-5) per 100 parts by weight of the matrix monomer and mechanical properties.

TABLE 6

| Example No. | Kind of inorganic filler | Blending ratio inorganic filler (pts. by wt.) | Fracture toughness value (Mpa · m$^{1/2}$) | Bending strength (Mpa) |
| --- | --- | --- | --- | --- |
| 1 | M-5 | 567 | 2.3 | 225 |
| 2 | M-6 | 426 | 1.7 | 195 |
| 3 | M-7 | 681 | 2.3 | 227 |
| 4 | M-8 | 462 | 2.0 | 210 |
| 5 | M-9 | 449 | 2.0 | 215 |
| 6 | M-10 | 609 | 2.3 | 220 |

(Comparative Examples 2 to 6)

Curable compositions were obtained in the same manner as in Comparative Example 1 but changing the inorganic filler blended in Comparative Example 1 as shown in Table 6. Table 6 shows the blending ratios of the inorganic fillers per 100 parts by weight of the matrix monomer and mechanical properties.

We claim:
1. A curable composition comprising:
 (i) a polymerizable monomer;
 (ii) irregular-shaped inorganic particles (A) having an average particle diameter of from 1 to 9 μm, and containing particles having particle diameters of not smaller than 10 μm in an amount of not larger than 3% by weight;
 (iii) spherical inorganic particles (B) having an average particle diameter of from 0.1 to 5 μm;
 (iv) inorganic fine particles (C) having an average particle diameter of from 0.01 to 0.1 μm; and
 (v) a polymerization initiator;
 wherein the irregular-shaped inorganic particles (A), spherical inorganic particles (B) and inorganic fine particles (C) are used in a total amount of from 300 to 1900 parts by weight per 100 parts by weight of the polymerizable monomer, and, when the total amount of the spherical inorganic particles (B) and the inorganic fine particles (C) is set to be 100% by weight, the spherical inorganic particles (B) are used at a ratio of from 50 to 99% by weight and the inorganic fine particles (C) are used at a ratio of from 50 to 1% by weight, and wherein the weight ratio [(A)/{(B)+(C)}] of the irregular-shaped inorganic particles (A) to the total amount of the spherical inorganic particles (B) and the inorganic fine particles (C) is from 0.3 to 3, and the polymerization initiator is blended in an amount of from 0.01 to 5 parts by weight per 100 parts by weight of the polymerizable monomer.

2. A curable composition according to claim 1, wherein the irregular-shaped inorganic particles (A) have an average particle diameter of from 1.5 to 5 μm and contains particles having diameters of not smaller than 10 μm in an amount of not larger than 1% by weight.

3. A curable composition according to claim 1, wherein the spherical inorganic particles (B) have an average degree of symmetry of not smaller than 0.6.

4. A curable composition according to claim 1, wherein the inorganic fine particles (C) are spherical fine particles.

5. A curable composition according to claim 1, wherein the total amount of the irregular-shaped inorganic particles (A), spherical inorganic particles (B) and inorganic fine particles (C) is from 500 to 1200 parts by weight per 100 parts by weight of the polymerizable monomer, and when the total amount of the spherical inorganic particles (B) and the inorganic fine particles (C) is set to be 100% by weight, the amount of the spherical inorganic particles (B) is from 60 to 90% by weight and the amount of the inorganic fine particles (C) is from 40 to 10% by weight, and the weight ratio [(A)/{(B)+(C)}] of the irregular-shaped inorganic particles (A) to the total amount of the spherical inorganic particles (B) and the inorganic fine particles (C) is from 0.4 to 2.3.

6. A curable composition according to claim 1, wherein the irregular-shaped inorganic particles (A) consist chiefly of silica-zirconia, the spherical inorganic particles (B) consist chiefly of silica-zirconia, and the inorganic fine particles (C) consist chiefly of at least one inorganic oxide selected from the group consisting of silica, alumina, silica-zirconia and silica-titania.

7. A curable composition according to claim 1, wherein when the irregular-shaped inorganic particles (A), spherical inorganic particles (B) and inorganic fine particles (C) are mixed together, the integrated volume of the strongly aggregated pores having porous diameters of not smaller than 0.08 μm is not larger than 0.1 cc/g.

8. A curable composition according to claim 1, wherein the polymerizable monomer is a (meth)acrylate monomer having acryloyl groups and/or methacryloyl groups.

9. A curable composition according to claim 1, wherein said irregular-shaped inorganic particles (A), spherical inorganic particles (B) and inorganic fine particles (C) are mixed together in advance, and the polymerizable monomer and the polymerization initiator are blended with said mixture.

10. A curable composition comprising:
 (i) a polymerizable monomer;
 (ii) amorphous inorganic particles (A) consisting chiefly of silica-zirconia and having an average particle diameter of from 1 to 9 μm, and containing particles having particle diameters of not smaller than 10 μm in an amount of not larger than 3% by weight;

(iii) spherical inorganic particles (B) consisting chiefly of silica-zirconia and having an average particle diameter of from 0.1 to 5 μm;

(iv) inorganic fine particles (C) consisting chiefly of at least one inorganic oxide selected from the group consisting of silica, alumina, silica-zirconia, and silica-titania and having an average particle diameter of from 0.01 to 0.1 μm; and (v) a polymerization initiator;

wherein the irregular-shaped inorganic particles (A), spherical inorganic particles (B) and inorganic fine particles (C) are used in a total amount of from 500 to 1200 parts by weight per 100 parts by weight of the polymerizable monomer, and, when the total amount of the spherical inorganic particles (B) and the inorganic fine particles (C) is set to be 100% by weight, the spherical inorganic particles (B) are used in an amount of from 60 to 90% by weight and the inorganic fine particles (C) are used in an amount of from 40 to 10% by weight, the weight ratio [(A)/{(B)+(C)}] of the irregular-shaped inorganic particles (A) to the total amount of the spherical inorganic particles (B) and the inorganic fine particles (C) is from 0.7 to 1.5, and wherein the irregular-shaped inorganic particles (A), spherical inorganic particles (B) and inorganic fine particles (C) in a state of being mixed together have an integrated volume of strongly aggregated pores having pore diameters of not smaller than 0.08 μm of not larger than 0.1 cc/g, and the polymerization initiator is used in an amount of from 0.01 to 5 parts by weight per 100 parts by weight of the polymerizable monomer.

\* \* \* \* \*